(12) United States Patent
Sherman

(10) Patent No.: US 6,667,054 B2
(45) Date of Patent: Dec. 23, 2003

(54) METFORMIN HYDROCHLORIDE TABLETS

(75) Inventor: Bernard Charles Sherman, 50 Old Colony Rd., Willowdale, Ontario (CA), M2L 2K1

(73) Assignee: Bernard Charles Sherman, Willowdale (CA)

( * ) Notice: Subject to any disclaimer, the term of this patent is extended or adjusted under 35 U.S.C. 154(b) by 0 days.

(21) Appl. No.: 10/002,130

(22) Filed: Dec. 5, 2001

(65) Prior Publication Data

US 2003/0104049 A1 Jun. 5, 2003

(51) Int. Cl.$^7$ .................................................. A61K 9/20
(52) U.S. Cl. .......................... 424/464; 424/465; 514/781
(58) Field of Search .................................. 424/464, 465

(56) References Cited

U.S. PATENT DOCUMENTS 6,117,451 A  *  9/2000  Kumar ........................ 424/465
6,340,475 B2 *  1/2002  Shell et al. .................. 424/469

* cited by examiner

Primary Examiner—James M. Spear
(74) Attorney, Agent, or Firm—Neil H. Hughes; Ivor M. Hughes; Marcelo K. Sarkis

(57) ABSTRACT

Tablets for oral administration comprising metformin hydrochloride and methylcellulose.

20 Claims, No Drawings

METFORMIN HYDROCHLORIDE TABLETS

BACKGROUND OF THE INVENTION

Metformin hydrochloride is an orally-administered antihyperglycemic agent, used in the management of non-insulin-dependent diabetes mellitus.

Metformin hydrochloride tablets are sold in strengths of 500 mg, 850 mg and 1000 mg in the United States and elsewhere under the tradename Glucophage™.

Glucophage™ tablets are made as core tablets comprising metformin hydrochloride, povidone and magnesium stearate, which are then film-coated. For the 1000 mg strength of Glucophage™ tablets, the weight per tablet is about 1070 mg, of which the weight of the core tablet before coating is about 1050 mg.

The function of the magnesium stearate in the core tablet is to act as a lubricant to prevent sticking to the tooling (punches and dies) in the tabletting process. The function of the povidone is to act as a binder to cause the metformin hydrochloride to bind into a sufficiently hard tablet under compression in the tabletting process.

In general, pharmaceutical tablets are made either by a "dry-mix" process or a "wet-granulation" process.

In a dry-mix process, ingredients are mixed together in dry form (i.e. without addition of water or an organic solvent) and the mixture is then either directly compressed into tablets, or alternatively compacted into slugs, which are then ground up into granules, following which the granules are then compressed into tablets.

™-Registered trademark

A dry-mix process is possible only when either:

i) the active ingredient itself has suitable binding properties to enable binding into hard tablets on compression, or ii) a sufficient quantity of a dry-mix binder can be mixed with the active, so that the mixture will form hard tablets on compression. There are numerous inactive ingredients that are frequently used as dry-mix binders, such as, for example, microcrystalline cellulose, dicalcium phosphate and lactose. Microcrystalline cellulose is generally considered to be the best dry-mix binder, in that it enables increased tablet hardness when used in relatively small amount.

Metformin hydrochloride is an active ingredient which does not have good binding properties. Hence, dry-mix tablets are only possible if enough of a dry-mix binder can be added to enable tablets of adequate hardness to be made. For metformin hydrochloride, the amount of microcrystalline cellulose that needs to be added to enable tablets of adequate hardness is about 500 mg or more per 1000 mg of metformin hydrochloride. A tablet comprising 1000 mg of metformin hydrochloride would thus need to weigh about 1500 mg or more, and would be of size difficult to swallow. It is apparently for this reason that Glucophage™ tablets are not made by the dry-mix approach.

When a dry-mix approach cannot be used, the alternative is "wet granulation".

This approach uses a binder that is more effective than microcrystalline cellulose on an equal-weight basis, but such binders need to be activated by use of a solvent. That is to say, the binder and water or organic solvent are mixed with the active ingredient, with or without other excipients (inactive ingredients) to form a wet mass, the wet mass is dried to evaporate the solvent, the dried mass is ground up into granules. Other excipients (including a lubricant) are then added, and the mixture is compressed into tablets. Commonly used wet-granulation binders are povidone, hydroxypropyl cellulose, pregelatinized starch and gelatin.

Glucophage™ tablets are made by the wet-granulation approach using povidone as the binder, and magnesium stearate as lubricant. This approach enables tablets of adequate hardness with minimum weight and size. However, this approach has the disadvantage of being relatively complex, in that the process requires the steps of adding water or another solvent to activate the binder and evaporating the solvent.

In light of this prior art, the object of the present invention is to enable the manufacture of metformin hydrochloride tablets of relatively small size by a dry-mix process; that is to say, a process that does not include the addition of water or another solvent to activate the binder.

BRIEF SUMMARY OF THE INVENTION

It has surprisingly been found that metformin hydrochloride tablets of relatively small size and good hardness can be made by a dry-mix process using methylcellulose as a dry-mix binder, provided that no stearate is added, or alternatively the amount of stearate that is added is under 0.6% by weight.

DETAILED DESCRIPTION OF THE INVENTION

As aforesaid, a "dry-mix" process is to be understood to be a process in which the ingredients are mixed together in dry form in one or more steps, without the addition of water or another solvent to activate a binder.

Tablets according to the present invention will comprise metformin hydrochloride as active ingredient and methylcellulose as dry-mix binder.

The quantity of metformin hydrochloride per tablet will be from 250 mg to 1000 mg.

Methylcellulose suitable for use in tablets of the invention is available from Dow Chemical Company under the tradename Methocel™. It is available in viscosity grades of 15 cps, 400 cps, 1500 cps and 4000 cps, for 2% solutions in water at 20° C.

The quantity of methylcellulose in the tablets by weight will be preferably from 0.05 to 0.5 part per part metformin hydrochloride, more preferably from 0.05 to 0.4 part per part metformin hydrochloride, even more preferably from 0.1 to 0.3 part per part metformin hydrochloride, still more preferably from 0.1 to 0.25 part per part metformin hydrochloride, and most preferably from 0.1 to 0.2 part per part metformin hydrochloride.

Accordingly, in a tablet comprising 1000 mg metformin hydrochloride, the amount of methylcellulose will be preferably from 50 mg to 500 mg, more preferably from 56 mg to 400 mg, even more preferably from 100 mg to 300 mg, still more preferably from 100 mg to 250 mg, and most preferably from 100 mg to 200 mg.

The tablets of the present invention will optionally also comprise a lubricant to avoid sticking to the tooling in the tabletting process.

The lubricants most commonly used in pharmaceutical tablets are stearates, by which is meant salts of stearic acid, such as, for example magnesium stearate and calcium stearate. Furthermore, among stearates, the lubricant most frequently used is magnesium stearate, usually at a level of from about one percent to about two percent by weight.

™-Registered trademark

However, in order to achieve satisfactory hardness and low friability, tablets of the present invention, will preferably be free of stearate, or alternatively will comprise a stearate at a level of less than 0.6 percent by weight. Where a stearate is used, the amount will be preferably from 0.01% to 0.59% by weight, more preferably from 0.01% to 0.4% by weight, even more preferably from 0.01% to 0.3% by weight, still more preferably from 0.01% to 0.2% by weight, and most preferably from 0.01% to 0.1% by weight.

Where a stearate is used, the stearate will preferably be magnesium stearate.

Tablets of the present invention will be made by a dry-mix process as previously defined.

The invention will be further understood from the following examples, which are intended to be illustrative and not limiting of the invention.

|  | Example No. | | | | | |
| --- | --- | --- | --- | --- | --- | --- |
|  | 1 | 2 | 3 | 4 | 5 | 6 |
| Metformin Hydrochloride | 1000. | 1000. | 1000. | 1000. | 1000. | 1000. |
| Methylcellulose 15CPS | 172. | 176. | 178. | 179. | 180. | 0. |
| Microcrystalline Cellulose | 0. | 0. | 0. | 0. | 0. | 180. |
| Magnesium Stearate | 8. | 4. | 2. | 1. | 0. | 0. |
|  | 1180. | 1180. | 1180. | 1180. | 1180. | 1180. |

For each of the examples, the ingredients were mixed together in dry form (i.e. without addition of water or any other solvent). The powder mixture was then compressed into slugs (i.e. large tablets) on a tablet press. The slugs were then milled into granules. The granules were then recompressed into tablets of unit weight 1180 mg, using 0.345 inch×0.748 inch modified-oval shaped tooling, at high pressure.

Sample tablets of each example were then tested for hardness using a Vankel™ model 40-2000 hardness tester, and for friability using a friabilator meeting the specifications of the United States Pharmacopoeia.

The average results for each example were as follows:

|  | Example No. | | | | | |
| --- | --- | --- | --- | --- | --- | --- |
|  | 1 | 2 | 3 | 4 | 5 | 6 |
| Hardness (Kp) | 3.6 | 7.3 | 7.8 | 10.7 | 19.6 | 7.9 |
| Friability in 5 minutes | all broken | 1.9% | 0.9% | 0.8% | 0.2% | all broken |

All of examples 1 to 5 have from about 0.17 to 0.18 part methylcellulose per part metformin hydrochloride, with magnesium stearate from about 0.68% in example 1 reducing to none in example 5. It can be seen that, as the amount of magnesium stearate is reduced in these examples, the hardness and friability are dramatically improved.

For example 6, in which microcrystalline cellulose is used as dry-mix binder instead of methylcellulose, the hardness is lower than that of examples 4 and 5 and the friability is much worse, despite the absence of magnesium stearate.

™-Registered trademark

What is claimed is:

1. A tablet for oral administration comprising metformin hydrochloride, and further comprising from 0.05 to 0.5 part methylcellulose per part metformin hydrochloride by weight, wherein said tablet is free of stearate or further comprises less than 0.6% stearate by weight.

2. A tablet of claim 1 comprising from 0.05 to 0.4 part methylcellulose per part metformin hydrochloride by weight.

3. A tablet of claim 1 comprising from 0.1 to 0.3 part methylcellulose per part metformin hydrochloride by weight.

4. A tablet of claim 1 comprising from 0.1 to 0.25 part methylcellulose per part metformin hydrochloride by weight.

5. A tablet of claim 1 comprising from 0.1 to 0.2 part methylcellulose per part metformin hydrochloride by weight.

6. A tablet for oral administration comprising 1000 mg of metformin hydrochloride and further comprising from 50 mg to 500 mg methylcellulose, wherein said tablet is free of stearate or further comprises less than 0.6% stearate by weight.

7. A tablet of claim 6 comprising from 50 mg to 400 mg methylcellulose.

8. A tablet of claim 7 comprising from 100 mg to 300 mg methylcellulose.

9. A tablet of claim 6 comprising from 100 mg to 250 mg methylcellulose.

10. A tablet of claim 6 comprising from 100 mg to 200 mg methylcellulose.

11. A tablet for oral administration comprising 1000 mg of metformin hydrochloride, from 0.05 to 0.5 part methylcellulose per part metformin hydrochloride by weight, wherein said tablet is free of stearate or comprising less than 0.6% stearate by weight.

12. A tablet of claim 1 that is free of stearate.

13. A tablet of claim 1 that comprises from 0.01% to 0.59% stearate by weight.

14. A tablet of claim 1 that comprises from 0.01% to 0.4% stearate by weight.

15. A tablet of claim 1 that comprises from 0.01% to 0.3% stearate by weight.

16. A tablet of claim 1 that comprises from 0.01% to 0.2% stearate by weight.

17. A tablet of claim 13 that comprises from 0.01% to 0.1% stearate by weight.

18. A tablet of claim 13 wherein the stearate is magnesium stearate.

19. A tablet of claim 1 made by a dry-mix process.

20. A process of making a tablet of claim 1 that comprises one or more steps of mixing the ingredients in dry form, without the addition of water or organic solvent to activate a binder.

\* \* \* \* \*